United States Patent
Zhmak et al.

(10) Patent No.: US 9,550,808 B2
(45) Date of Patent: Jan. 24, 2017

(54) PEPTIDE INHIBITORS OF NICOTINIC ACETYLCHOLINE RECEPTOR

(71) Applicant: LIMITED LIABILITY COMPANY SYNEURO, Moscow (RU)

(72) Inventors: Maxim Nurgayanovich Zhmak, Moscow (RU); Yury Nikolaevich Utkin, Moscow (RU); Tatyana Viktorovna Andreeva, Moscow (RU); Denis Sergeevich Kudryavtsev, Arhangel'skaya oblast' (RU); Elena Viktorovna Kryukova, Moscow (RU); Viktor Ionovich Tsetlin, Moscow (RU); Igor Evgen'evich Kasheverov, Moscow (RU); Vladislav Gennad'evich Starkov, Moscow (RU); Irina Valer'evna Shelukhina, Moscovskaya oblast' (RU)

(73) Assignee: Syneuro LLC, Moscow (RU)

( * ) Notice: Subject to any disclaimer, the term of this patent is extended or adjusted under 35 U.S.C. 154(b) by 0 days.

(21) Appl. No.: 14/762,177

(22) PCT Filed: Jan. 20, 2014

(86) PCT No.: PCT/RU2014/000032
§ 371 (c)(1),
(2) Date: Jul. 20, 2015

(87) PCT Pub. No.: WO2014/112902
PCT Pub. Date: Jul. 24, 2014

(65) Prior Publication Data
US 2015/0361137 A1    Dec. 17, 2015

(30) Foreign Application Priority Data
Jan. 21, 2013 (RU) .................. 2013102410

(51) Int. Cl.
| | | |
|---|---|---|
| A61K 9/127 | (2006.01) |
| A61K 38/00 | (2006.01) |
| A61P 17/00 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 7/06 | (2006.01) |
| A61Q 19/08 | (2006.01) |
| A61K 8/64 | (2006.01) |
| C07K 14/705 | (2006.01) |

(52) U.S. Cl.
CPC . *C07K 7/06* (2013.01); *A61K 8/64* (2013.01); *A61Q 19/08* (2013.01); *A61K 38/00* (2013.01); *C07K 14/70571* (2013.01)

(58) Field of Classification Search
CPC .................................. C07K 7/02; A61K 38/08
See application file for complete search history.

(56) References Cited

U.S. PATENT DOCUMENTS

2009/0111731 A1    4/2009    Imfeld et al.

OTHER PUBLICATIONS

Utkin et al. "Azemiopsin from Azemiops feae Viper Venom, a Novel Polypeptide Ligand of Nicotinic Acetylcholine Receptor" J. Biol. Chem. 287:27079-27086. Published May 21, 2012.*
Van Damme et al. "NatF Contributes to an Evolutionary Shift in Protein N-termianl Acetylation and Is Important for Normal Chromosomal Segregation" PLoS Genetics 7:e1002169. Published Jul. 7, 2011.*
Kim and Seong "Peptide Amidation: Production of Peptide Hormones in vivo and in vitro" Biotechnol. Bioprocess Eng. 6:244-251. Published 2001.*
International Search Report of PCT/RU2014/000032 dated Jun. 10, 2014.
Utkin Y.N. et al. Azemiopsin from Azemiops feae Viper Venom, a Novel Polypeptide Ligand of Nicotinic Acetylcholine Receptro, J. Biol. Chem., vol. 287, No. 32, pp. 27079-27086, 2012.

* cited by examiner

*Primary Examiner* — Christina Bradley
*Assistant Examiner* — Zachary J Miknis
(74) *Attorney, Agent, or Firm* — Arent Fox LLP; Michael Fainberg

(57) ABSTRACT

The present invention refers to biochemistry, namely to new peptide compounds having the ability to selectively block the muscle-type nicotinic acetylcholine receptor. The claimed compounds have common formula (I): X1-X2-X3-Pro-X4-Pro-X5 (SEQ ID NO: 54), where X1 is chosen within H, Ac—, Palm-; X2 is chosen within Trp, Tyr; X3 is chosen within Trp, Tyr; X4 is chosen within Lys, Orn, Dbu, Dpr, Arg; X5 is chosen within —OH, —NH$_2$, —OCH$_3$, —OC$_2$H$_5$, —NH—C$_6$H$_5$. The invention can be applied in cosmetics for smoothing mimic and age-related Wrinkles.

10 Claims, 6 Drawing Sheets

PEPTIDE INHIBITORS OF NICOTINIC ACETYLCHOLINE RECEPTOR

CROSS-REFERENCE TO RELATED APPLICATION

This application is a National Stage entry of International Application No. PCT/RU2014/000032, filed Jan. 20, 2014, which claims priority to Russian Patent Application No. 2013102410, filed Jan. 21, 2013. The disclosures of the priority applications are incorporated in their entirety herein by reference.

SEQUENCE LISTING

The instant application contains a Sequence Listing which has been submitted electronically in ASCII format and is hereby incorporated by reference in its entirety. Said ASCII copy, created on Jul. 17, 2015, is named 036933.00001_SL.txt and is 19,456 bytes in size.

TECHNICAL FIELD

The present invention relates to biochemistry namely to new peptide compounds able to selectively block the muscle-type nicotinic acetylcholine receptor. More particularly the invention relates to applying those compounds for smoothing mimic and age-related wrinkles.

BACKGROUND ART

In the last decades the steady increased expectation of life in developed countries has been observed. In 2000 in the USA there were 13% of people older than 65 years, in 2030 the number is being expected to increase up to 20%. The demographical change demands accelerating efforts to design an effective medical treatment for senior people. This demand refers in full measure to the cosmetic dermatology which provides with roborant, anti-aging and sun-protecting agents as well as anti-wrinkle creams. Cosmetic and pharmaceutical companies often use peptides as active ingredients in such creams. Peptides and the cosmetics on their basement have different activity: stimulation of fibroblast activity, inhibiting of the enzymes involved in collagen degradation, angiogenesis stimulation, immunomodulating, regulating melanin production, neuromuscular transmission blockage. One of the most important drawbacks for topical application of the peptides in creams is their decreased ability to penetrate into the skin. In fact, the ability to penetrate into the skin depends on various factors such as physical and chemical conditions of the compound (dissociation constant [pKa], molecular size, stability, solubility and lipophilicity coefficient); penetrating time; sustainability, thickness and skin composition, skin metabolism; area, square and duration of the application (Ranade, V. V. Drug delivery systems. 6. Transdermal drug delivery. J. Clin. Pharmacol. 1991, 31, 401-418). A peptide is considered to be a suitable tool for topical application if it corresponds to the parameters listed below, however, it must be noted that all the parameters are empirical and not universal (Guy, R. H. Current status and future prospects of transdermal drug delivery. Pharm. Res. 1996, 13, 1765-1769):
1. Molecular mass less than 500 Da
2. Lipophilic coefficient value (logarithm of the distribution coefficient for the octanol/water system) from 1 to 3.
3. Melting temperature under 200 C.
4. Good solubility in water (1 mg/ml)
5. No or few polar centers.

Peptides used in cosmetology can be divided into four major groups: signal peptides, enzyme inhibitors, carrier peptides and blockers of neuromuscular transmission (Gorouhi F, Maibach H I. Role of topical peptides in preventing or treating aged skin. Int J Cosmet Sci. 2009 October; 31(5):327-45). Despite the similar visible physiological effect after using the peptides from the four groups, the mechanism of their action differs significantly. The peptides from the group of blockers of neuromuscular transmission are therewith considered as a safe alternative for botulotoxin injections used for treatment of age-related and mimic wrinkles. Highly specific botox has many drawbacks such as high toxicity and therefore, the necessity of the exact dose amount calculation, essential dependence of product quality on manufacturing conditions, injected usage only.

Muscle contraction is a physiological process under which muscles undergo tension—shorten or lengthen providing mechanical work. This process provides animals and humans with the ability to spontaneous and nonspontaneous movements and directly connected with digestive, respiratory, defensive, secretory and other physiological processes. Unstriated muscle is responsible for nonspontaneous movement, for example ventricle or intestinal peristalsis, changes in tonus of blood vessels and urinary bladder. Striated muscle provides spontaneous movement—spatial motion, face mimics, breath, swallowing etc. Heart work is provided by the heart muscular contraction.

Muscles are formed by multinuclear muscular fibers each of them separately is not only cellular but also physiological unit owning to the presence of such a specific "contracting" element as myofibrils. Those filaments are gathered into the clusters of the first order; several first-order clusters combine and form clusters of the second order etc. leading to the muscle formation. As muscle contraction is initiated by an impulse coming from the central nervous system, there are areas on the muscle which are innervated with synaptic terminals of neuronal axons. The junction between the neuron and muscle fiber is called neuromuscular synapse (NMS).

The mechanism of muscle contraction can be divided into several main stages. The first stage is sending a stimulus from neurons in a form of action potential. Action potential spreads along the nerve fibril to its terminals on the muscle fibers which leads to acetylcholine (Ach) neurotransmitter release from the presynaptic part of NMS into the synaptic gap. This neurotransmitter affects only a part of the muscle fiber membrane (postsynaptic part of NMS) opening various acetylcholine gated channels—acetylcholine receptors (AChRs). In response to the opening of the channels, there is an increase in sodium concentration inside the muscle fiber that leads to generation of action potential on cell membrane which is conducted longwise the muscle fiber membrane. Action potential depolarizes muscle membrane leading to calcium ions release from sarcoplasmic reticulum. Calcium ions directly initiate the process of muscle contraction. By means of calcium pump, calcium is actively pumped back into the sarcoplasmic reticulum leading to muscle relaxation.

The mechanism of acetylcholine release is well established. When neuronal impulse in a form of action potential reaches the termini of the motor neurons it opens calcium channels located on the presynaptic membrane of NMS. Local increase in intracellular calcium ion concentration is followed by calcium interaction with the proteins which provide fusion of synaptic vesicles containing neurotransmitter Ach with the plasma membrane. The process has also been studied in details and goes with the help of complex SNARE formed by the effective four-helix junction of three proteins—vesicle surface protein synaptobrevin, syntaxin and neuronal surface membrane protein SNAP-25. The complex formation leads to rapid fusion of the vesicle and plasma membranes and induces exocytosis of Ach into the synaptic gap. Ach molecules defuse throughout the gap with width 50-100 nm and reach postsynaptic membrane which is very sensitive to the transmitter due to the presence of highly specific receptors—AchRs. Their binding with Ach initiates opening of the channel; it causes dramatic influx of sodium inside the cell and a weaker flow of potassium out of the cell with the further depolarization of muscular membrane, calcium release and muscle contraction as described above.

The mechanism of neuronal impulse transmission through the postsynaptic part of NMS resulting from the binding of meurotransmitter Ach to the AChR and was also well studied. There are two major groups of AChRs—nicotinic (nAChRs) and muscarinic (mAChRs) which differ in their ability to bind with agonists. In particular, nAChRs were named for their ability to bind a natural plant alkaloid nicotine, and mAChRs—for the ability to bind muscarine alkaloid from poisonous mushrooms. NAChRs are ionotropic receptors which are permeable for specific ions after binding with a ligand. MAChR refers to a group of metabotropic receptors; it is a one-chain protein containing 7 transmembrane fragments associated with G-pritein. In this case, signal transmission after ligand binding follows many metabolic pathways.

At the molecular level nAChRs are oligomeric proteins consisting of 5 subunits. In membranes the 5 subunits are known to be pseudo symmetrically organized around the central axis where there is an ionic channel with diameter of 2.5 nm. These data were obtained for nAChR from the electrical organ of the electric ray Torpedo; this receptor has subunit composition $(\alpha 1)_2$-$\beta 1$-$\gamma$-$\delta$ [Unwin N. Refined structure of the nicotinic acetylcholine receptor at 4 Å resolution. J Mol Biol 2005; 346: 967-89]. Up to present, 10 various subtypes of α-subunits (α1-α10) and 4 β subunits (β1-β4) are discovered. All the subtypes of α- and β-subunits (except α1- and β1-) are revealed in neuronal type nAChRs expressed mainly in neurons of the central and/or peripheral nervous system in many cases even on the presynaptic membrane [Dani J A, Bertrand D. Nicotinic acetylcholine receptors and nicotinic cholinergic mechanisms of the central nervous system. Annu Rev Pharmacol Toxicol 2007; 47: 699-729]. Postsynaptic nAChRs of both animal and human neuromuscular synapses have composition $(\alpha 1)_2$-$\beta 1$-$\gamma$-$\delta$ (identical to the one for the receptor from electrical organ) but at the stage of the initial (embryotic) development of an organism. In the mature form γ-subunit is substituted with ε-[Yomoto N., Wakatsuki S., Sehara-Fujisawa A. 2005. The acetylcholine receptor gamma-to-epsilon switch occurs in individual endplates. Biochem. Biophys. Res. Commun 331: 1522-1527]. In the mature muscle, only nAChR with the structure $(\alpha 1)_2$-$\beta 1$-$\epsilon$-$\delta$ is responsible for binding the neurotransmitter which leads to muscle contraction. Taking into account the highly homologous structure of all the nAChR sunbunits, their spatial pentameric channel composition in the membrane is considered to be similar too. Nowadays the nAChRs region for binding with the classical agonists and competitive antagonists is also discovered: two ligand binding regions are located in the area of the contact of major N-terminal extracellular domains of two α1-and neighboring γ(ε)- and δ-subunits of the receptor approximately in the middle part towards the membrane surface.

To provide the neuron and the muscle fiber with the fast information transmission, high concentration of AChR in essential areas of postsynaptic membrane of neuromuscular junction is needed. Therefore, aggregation of AChRs is crucial for normal functioning of neuromuscular junction [Hoch W. 1999. Formation of the neuromuscular junction. Agrin and its unusual receptors. Eur. J. Biochem. 265:1-10]. There are several proteins involved in the process of aggregation, mainly agrin, rapsin and kinase MuSK (Muscle-Specific Kinase). Developed earlier and being created nowadays new agents blocking neuromuscular transmission are aimed at disruption of normal functioning of either presynaptic membrane of NMS or postsynaptic part of a synapse.

Cosmetic industry has undertaken several various efforts to develop new compounds for the topic application during the treatment of mimic wrinkles to avoid side effects observed after botulinum toxin injections (Lupo M P, Cole A L. Cosmeceutical peptides. Dermatol Ther. 2007, September-October;20(5):343-9). Up to present, several peptide compounds are known to block neuromuscular transmission (Table 1)

TABLE 1

Amino acid sequence of the peptides blocking neuromuscular transmission, and their biological activities.

| Name | Amino acid sequence | Activity |
| --- | --- | --- |
| Argireline | Ac-Glu-Glu-Met-Gln-Arg-Arg-NH2 (SEQ ID NO: 49) | Inhibits formation of the complex SNARE and neurotransmitter release |
| Leuphasyl | H-Tyr-D-Ala-Gly-Phe-Leu-OH | Mimics the action of enkefalin - decreases neuronal excitation |
| Vialox | H-Gly-Pro-Arg-Pro-Ala-NH2 (SEQ ID NO: 50) | Competitive antagonist of nAChR |
| Syn-Ake | H-β-Ala-Pro-Dab-NHBzl | Competitive antagonist of nAChR |
| Inyline | not published | Competitive antagonist of MuSK |

Peptide argireline is the top one within "cosmetic analogues of botox" (Blanes-Mira C., et al. A synthetic hexapeptide (Argireline) with anti-wrinkle activity. Int J Cosmet Sci. 2002; 24(5): 303-310). Appearing at the beginning of 2000, it rapidly gained the popularity—today it is used in many cosmetic drugs aimed at smoothing mimic wrinkles. Six amino acids of argireline repeat the protein fragment SNAP 25 necessary for synaptic axonal vesicle binding with the presynaptic membrane. In an axon, argireline competes with protein SNAP25 and inserts into the temporary complex SNARE instead of it—this complex is formed from several membrane proteins directly before synapse binds with the membrane, and it is necessary for successful exocytosis. A deficient complex cannot provide a good junction of vesicle with membrane, as a result transmitter release does not occur and muscle does not receive a signal to contract and stay relaxed.

Argireline analogues obtained from protein SNAP 25 and aimed at inhibiting neuromuscular transmission at synaptic level by competing with SNAP 25 for complex SNARE formation, are described in patents EP 1180524 и WO9734620.

Topic 30-day use of cream containing 10% of argireline studied on volunteers leads to 30% decrease in the depth of mimic wrinkles in comparison with 10% exposure of Placebo. Pentapeptide Leuphasyl developed by Lipotech company (Spain) mimics enkephalin action decreasing neuronal excitation by inhibiting $Ca^{2+}$-influx throughout the membrane and decreasing $Ca^{2+}$-dependant transmitter release. Use of Leuphasyl in a combination with argireline enhances argireline effect by 1.5-fold.

Inyline is an acetyl hexapeptide developed by Lipotech company (Spain) (WO2011/009626) was created basing on the predicted structure of the binding area of agrin to MuSK (Muscle-Specific Kinase) obtained by molecular modeling. Inyline works as a competitive antagonist of MuSK at binding with agrin, which is essential for muscle contraction. Postsynaptic mechanism of decreasing muscle contraction helps to avoid appearance of mimic wrinkles. Studies on volunteers have shown that 28-day administration of 5% Inyline solution leads to reduction in the depth of the wrinkles in the area of "crows feet" on 14.9%.

Vialox (Pentapharm company, Switzerland) is a pentapeptide fragment of the neurotoxin waglerin-1 from the venom of the Temple Viper. Vialox has a curare-like activity and it is a competitive antagonist of the nAChR. When the peptide binds the receptor sodium ion channel keeps closed which disrupts neuronal impulse transmission and does not allow muscles to contract. Patent EP1809652 describes peptide antagonists of the acetylcholine receptor which work postsynaptically following the vaglerine-1-like mechanism by blocking neuronal transmission and preventing wrinkle appearance. Vialox can be used together with other cosmetic peptides (WO 2006/069608).

28-day application of the cream containing 5% Vialox reduces wrinkle size up to 49% and skin roughness up to 47%.

One more active cosmetic peptide Syn-ake (Pentapharm, Switzerland) is a reversible antagonist of the muscle-type nicotinic acetylcholine receptor (mnAChR). This tripeptide acts in a manner similar to waglerin-1, which prevents acetylcholine binding with the receptor and the channel activation. Therefore, the muscles stay relaxed (WO 2006/047900). The studies performed on volunteers showed that the 28-day application of the cream containing 4% Syn-Ake decreases depth of wrinkles on foreheads up to 52%.

Thus, the competitive antagonists of the mnAChR Vialox and Syn-Ake are the most effective peptides with anti-wrinkle activity.

However, none of the compounds developed by cosmetic or pharmaceutical companies can inhibit muscle contraction with the effectiveness similar to botulinum toxin. Therefore, the necessity for creating new compounds capable to inhibit muscular contraction and reaching better results in decreasing and emolliating wrinkles especially mimic ones, still exists.

DISCLOSURE OF INVENTION

In this description the abbreviations used for the amino acids follow the recommendations of IUPAC-IUB (Eur. J. Biochem., 1984, 138:9-37; J. Biol. Chem., 1989, 264:633-673). Thus, for example, Lys represents $NH_2$—$CH(CH_2$—$CH_2$—$CH_2$—$NH_2)$—COOH, Lys- represents $NH_2$—CH $(CH_2$—$CH_2$—$CH_2$—$NH_2)$—CO—, -Lys represents —NH—$CH(CH_2$—$CH_2$—$CH_2$—$NH_2)$—COOH, -Lys- represents —NH—$CH(CH_2$—$CH_2$—$CH_2$—$NH_2)$—CO—. Therefore, the hyphen, which represents the peptide bound, eliminates the OH in the carboxyl group of the amino acid when situated to the right of the symbol, and eliminates the H of the alpha-amino-group of the amino acid when situated to the left of the symbol.

The abbreviation Ac- represents acetyl group ($CH_3$—CO—) and Palm- represents palmitoyl group ($CH_3$—$(CH_2)_{14}$—CO—).

The abbreviation Orn represents amino acid ornitine, Dbu-2,4-diaminobutyric acid, Dpr-2,3-diaminopropanoic acid, —NH—$C_6H_5$-benzilamide.

The term "cosmetically acceptable salts" of peptides in the context of the present invention means salts recognized for their use in human beings and include salts formed after addition of either inorganic compounds for example, litium, sodium, calcium, potassium, magnesium, copper, zinc etc., or organic compounds, for example, ethylamine, diethylamine, ethylenediamine, ethanolamine, diethanolamine, arginine, lysine, or acid addition salts, for example, acetate, citrate, lactate, malonate, maleate, fumarate, benzoate, aspartate, glutamate, oleate, trifluoroacetate, oxalate, gluconate, or inorganic acids, for example, chloride, sulfate, borate, carbonate. Cosmetically acceptable salts of the peptides of the invention can be obtained by the standard methods (Berge S. M., Bighley L. D. and Monkhouse D. C. 1977, "Pharmaceutical Salts", J. Pharm. Sci. 66:1-19).

The present invention solves the problem of increasing the number of neuromuscular transmission peptide blockers applicable for use in cosmetology and dermatology. Syn-Ake and Vialox are the analogues of the claimed peptide acting in a similar mechanism. Both peptides have been developed by the Swiss company "Pentapharm" on the basis of 21 amino acid component waglerin-1 obtained from the venom of the Temple Viper. Waglerin-1 is known to block muscular nAChR, hence it has an antagonistic activity (Weinstein S. A. et al. Characterization and amino acid sequences of two lethal peptides isolated from venom of Wagler's pit viper, *Trimeresurus wagleri*. Toxicon. 1991; 29(2):227-36). Short peptides on its basement do not manifest toxicity and at high concentrations keep blocking the same receptor.

Recently (Utkin Y. N. et al. Azemiopsin from *Azemiops feae* Viper Venom, a Novel Polypeptide Ligand of Nicotinic Acetylcholine Receptor. J. Biol. Chem. 2012, August 3; 287(32):27079-86) polypeptide azemiopsin containing 21 amino acids (DNWWPKPPHQGPRPPRPRPKP (SEQ ID NO: 51)) has been discovered in the venom of the Fea's Viper. It is also able to block muscular nAChRs. While carrying out the search of an active center of azemiopsin (fragment of the amino acid sequence mainly contributing into the ability to bind the nAChR) using electrophysiological methods (FIG. 1), the range of overlapping pentapeptide fragments of the initial toxin was tested (FIG. 2). The ability to inhibit acetylcholine induced currents through the muscle-type AChR expressed in oocytes from the clawed frog *Xenopus laevis* was investigated. Preliminary tests of these fragments were carried out at concentration of 150 μg/ml. The results obtained are shown in FIG. 2. Pentapeptide SEQ ID NO:1:WWPKP appeared to be the most active. Meanwhile, this peptide does not exhibit toxicity at the doses up to 30 mg/kg at intraperitoneal injection and at the doses up to 160 mg/kg at per oral application. The sequence of pentapeptide fragment SEQ ID NO:1:WWPKP (hereafter Az3) was changed as described bellow: 1. Amid group is inserted at C-terminus (SEQ ID NO:41: H-Trp-Trp-Pro-Lys-Pro-NH$_2$, hereafter Az3-NH2); 2. Tryptophane residue was substituted with tyrosine residue: [Tyr1]Az3 (SEQ ID NO:3), [Tyr2]Az3 (SEQ ID NO:2) и [Tyr1,Tyr2]Az3 (SEQ ID NO:4); second amino acid residue was substituted with hydrophobic valine residue ([Val-2]Az3); 4. Lysine-4 was substituted for diaminobutyric acid SEQ ID NO:5: H-Trp-Trp-Pro-Dbu-Pro-OH ([Dbu4]Az3); 5. The peptide sequence was reduced to four and three amino acids:[des-Trp1]Az3, [des-Pro5]Az3, [des-Trp1,des-Pro5]Az3. Retrosequences of peptides Az3 and [Tyr2]Az3: PKPWW (SEQ ID NO: 52) and PKPYW (SEQ ID NO: 53) respectively have been synthesized and tested. However their inhibiting activity towards the muscle receptor was reduced. The diagram of retropeptides testing and comparison with the activity of initial Az3 and [Tyr2]Az3 is shown on FIG. 5. The peptides were tested in concentration of 1 mM.

Additional experiments were carried out to compare the effectiveness of the blockage of currents through the receptor channel by fragments of azemiopsin and commercial samples of Syn-Ake and Vialox. The compounds were tested at concentration of 1 mM. The results are shown on FIG. 3.

After performing the tests, it was established more appropriate to use an amid form of the pentapeptide fragment of azemiopsin with substitution of the second amino acid for tyrosine SEQ ID NO:42: H-Trp-Tyr-Pro-Lys-Pro-NH$_2$ (herein after [Tyr2]Az3-NH2).

For more detailed comparison of [Tyr2]Az3-NH2 with the most widespread commercial product Syn-Ake, the curves describing dependence of inhibiting activity on concentration were obtained as and shown in FIG. 3. Peptide [Tyr2]Az3-NH2 blocks 50% of current (value IC50) at the concentration of 23 μM, whereas the same concentration for Syn-Ake is equal to 180 μM, therefore, the new peptide is eight times more functionally active than the commercial analogue. It is demonstrated by a histogram on FIG. 5.

Compounds of the invention.

The task to obtain new compounds blocking mnAChR is achieved by means of the peptides with the structures described by the following formula (I): X1-X2-X3-Pro-X4-X5-X6 (SEQ ID NO: 54), where
X1 is selected from H, Ac- , Palm
X2 is selected from Trp, Tyr, His, Phe, Pro,
X3 is selected from Trp, Tyr, His, Phe, Lys, Orn, Dbu, Dpr, Arg
X4 is selected from Trp, Tyr, His, Phe, Lys, Orn, Dbu, Dpr, Arg
X5 is selected from Trp, Tyr, His, Phe, Pro
X6 is selected from —OH, —NH$_2$, —OCH$_3$, —OC$_2$H$_5$, —NH—C$_6$H$_5$ Preferably compounds of formula (I) are selected from the group containing:

| | | |
|---|---|---|
| SEQ ID NO: 1: | H-Trp-Trp-Pro-Lys-Pro-OH |
| SEQ ID NO: 2: | H-Trp-Tyr-Pro-Lys-Pro-OH |
| SEQ ID NO: 3: | H-Tyr-Trp-Pro-Lys-Pro-OH |
| SEQ ID NO: 4: | H-Tyr-Tyr-Pro-Lys-Pro-OH |
| SEQ ID NO: 5: | H-Trp-Trp-Pro-Dbu-Pro-OH |
| SEQ ID NO: 6: | H-Trp-Tyr-Pro-Dbu-Pro-OH |
| SEQ ID NO: 7: | H-Tyr-Trp-Pro-Dbu-Pro-OH |
| SEQ ID NO: 8: | H-Tyr-Tyr-Pro-Dbu-Pro-OH |
| SEQ ID NO: 9: | Ac-Trp-Trp-Pro-Lys-Pro-OH |
| SEQ ID NO: 10: | Ac-Trp-Tyr-Pro-Lys-Pro-OH |
| SEQ ID NO: 11: | Ac-Tyr-Trp-Pro-Lys-Pro-OH |
| SEQ ID NO: 12: | Ac-Tyr-Tyr-Pro-Lys-Pro-OH |
| SEQ ID NO: 13: | Ac-Trp-Trp-Pro-Dbu-Pro-OH |
| SEQ ID NO: 14: | Ac-Trp-Tyr-Pro-Dbu-Pro-OH |
| SEQ ID NO: 15: | Ac-Tyr-Trp-Pro-Dbu-Pro-OH |
| SEQ ID NO: 16: | Ac-Tyr-Tyr-Pro-Dbu-Pro-OH |
| SEQ ID NO: 17: | Ac-Trp-Trp-Pro-Lys-Pro-NH$_2$ |
| SEQ ID NO: 18: | Ac-Trp-Tyr-Pro-Lys-Pro-NH$_2$ |
| SEQ ID NO: 19: | Ac-Tyr-Trp-Pro-Lys-Pro-NH$_2$ |
| SEQ ID NO: 20: | Ac-Tyr-Tyr-Pro-Lys-Pro-NH$_2$ |
| SEQ ID NO: 21: | Ac -Trp-Trp-Pro-Dbu-Pro-NH$_2$ |
| SEQ ID NO: 22: | Ac-Trp-Tyr-Pro-Dbu-Pro-NH$_2$ |
| SEQ ID NO: 23: | Ac-Tyr-Trp-Pro-Dbu-Pro-NH$_2$ |
| SEQ ID NO: 24: | Ac-Tyr-Tyr-Pro-Dbu-Pro-NH$_2$ |
| SEQ ID NO: 25: | H-Trp-Trp-Pro-Lys-Pro-OCH$_3$ |
| SEQ ID NO: 26: | H-Trp-Tyr-Pro-Lys-Pro-OCH$_3$ |
| SEQ ID NO: 27: | H-Tyr-Trp-Pro-Lys-Pro-OCH$_3$ |
| SEQ ID NO: 28: | H-Tyr-Tyr-Pro-Lys-Pro-OCH$_3$ |
| SEQ ID NO: 29: | H-Trp-Trp-Pro-Dbu-Pro-OCH$_3$ |
| SEQ ID NO: 30: | H-Trp-Tyr-Pro-Dbu-Pro-OCH$_3$ |
| SEQ ID NO: 31: | H-Tyr-Trp-Pro-Dbu-Pro-OCH$_3$ |
| SEQ ID NO: 32: | H-Tyr-Tyr-Pro-Dbu-Pro-OCH$_3$ |
| SEQ ID NO: 33: | Ac-Trp-Trp-Pro-Lys-Pro-OCH$_3$ |
| SEQ ID NO: 34: | Ac-Trp-Tyr-Pro-Lys-Pro-OCH$_3$ |
| SEQ ID NO: 35: | Ac-Tyr-Trp-Pro-Lys-Pro-OCH$_3$ |
| SEQ ID NO: 36: | Ac-Tyr-Tyr-Pro-Lys-Pro-OCH$_3$ |
| SEQ ID NO: 37: | Ac-Trp-Trp-Pro-Dbu-Pro-OCH$_3$ |
| SEQ ID NO: 38: | Ac-Trp-Tyr-Pro-Dbu-Pro-OCH$_3$ |
| SEQ ID NO: 39: | Ac-Tyr-Trp-Pro-Dbu-Pro-OCH$_3$ |
| SEQ ID NO: 40: | Ac-Tyr-Tyr-Pro-Dbu-Pro-OCH$_3$ |
| SEQ ID NO: 41: | H-Trp-Trp-Pro-Lys-Pro-NH$_2$ |
| SEQ ID NO: 42: | H-Trp-Tyr-Pro-Lys-Pro-NH$_2$ |
| SEQ ID NO: 43: | H-Tyr-Trp-Pro-Lys-Pro-NH$_2$ |
| SEQ ID NO: 44: | H-Tyr-Tyr-Pro-Lys-Pro-NH$_2$ |
| SEQ ID NO: 45: | H-Trp-Trp-Pro-Dbu-Pro-NH$_2$ |
| SEQ ID NO: 46: | H-Trp-Tyr-Pro-Dbu-Pro-NH$_2$ |
| SEQ ID NO: 47: | H-Tyr-Trp-Pro-Dbu-Pro-NH$_2$ |
| SEQ ID NO: 48: | H-Tyr-Tyr-Pro-Dbu-Pro-NH$_2$ |

The peptides from the invention can consist of stereoisomers or mixures of stereoisomers of the amino acids, i.e. amino acids can have L- and/or D-configuration or exist as a racemic mixture independently in each position.

Technical result of the target invention is reached by means of such characteristics of the new peptide as: selective blockage of mnACChR, lack of toxic effects and lack of allergic reactions. As the size of the claimed peptides is small and they contain 5 amino acid residues they can be obtained by means of chemical synthesis. The claimed peptides are new compounds and do not have similar homologues.

The peptides can be used in cosmetology in a cosmetic composition in the form of cream, lotion or gel for face skin application for decreasing the depth of mimic and age-related wrinkles. Weight concentration of the peptide is within 0.01-5%. Except the compound with general formula (I) such cosmetic composition can contain at least one additional component chosen from: amino acids, proteins, protein hydrolysates, growth factors, enzymes, enzyme inhibitors, peptides, polysaccharides, pyrimidines, purines, nucleotides, nucleosides, carboxylic acids, fat acids, lipids, sphingolipids, flavonoids, phenols, polyphenols, terpenes, alkaloids, benzofurans, polyalcohols, antimicrobial component, antimicrobial peptides, vitamins, provitamins, retinoids, carotenoids, chelating agents, antioxidants, agents improving skin permeability.

MODES FOR CARRYING OUT THE INVENTION

EXAMPLE 1

Figure 1:
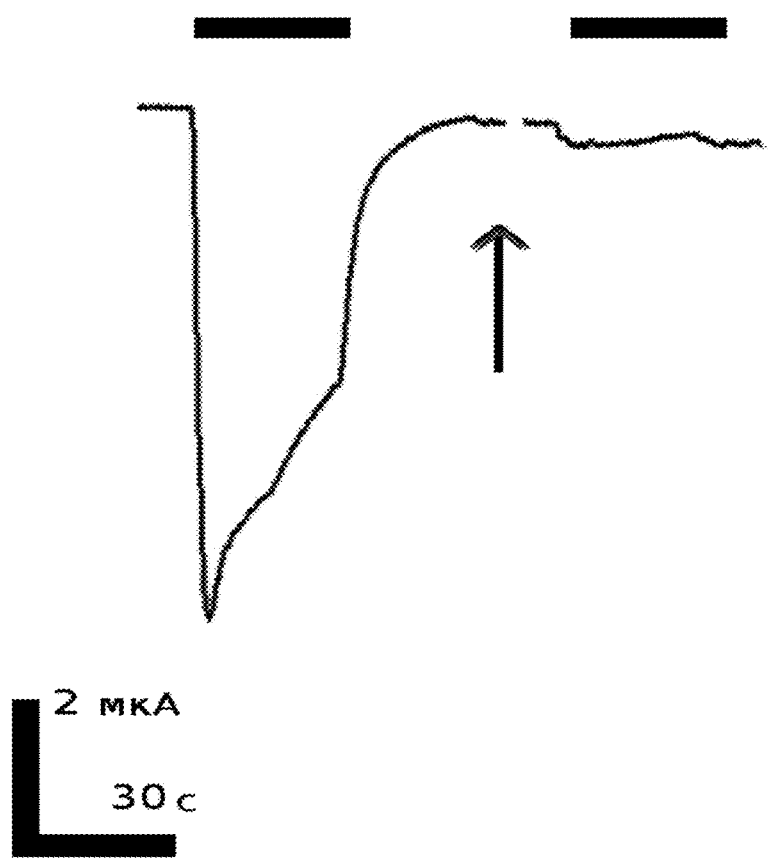
FIG. 1. Example of registration of the current through the muscle-type nAChR heterologously expressed in oocytes from clawed frog *Xenopus laevis*, in response to 20 μM acetylcholine application. Each application of acetylcholine in the presence of or without a ligand is marked with black square above. The control current, to the left end, is compared with the current obtained in the presence of 50 μM azemiopsin. The arrow shows the time of the beginning of incubation. Time interval between acetylcholine applications is 5 minutes. Complete blockage of the muscle receptor activity by azemiopsin is demonstrated.
Figure 2:
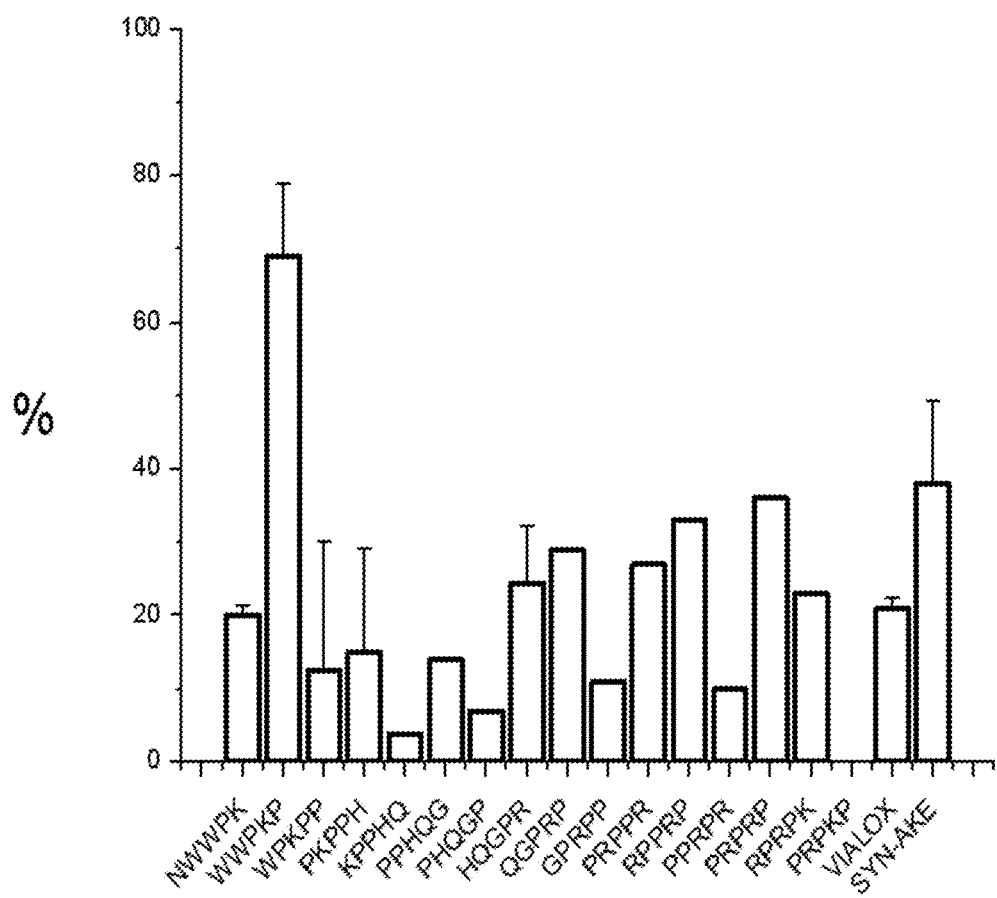
FIG. 2. Comparison of the effectiveness of the current inhibition through the muscle-type nAChR channel by overlapping pentameric fragments of azemiopsin and commercially available compounds Syn-Ake and Vialox (SEQ ID NOS 58, 1 and 59-72, respectively, in order of appearance). 100% refers to complete blockage of the current, 0% refers to the unblocked current. All the compounds are taken at concentration of 150 μg/ml.
Figure 3:
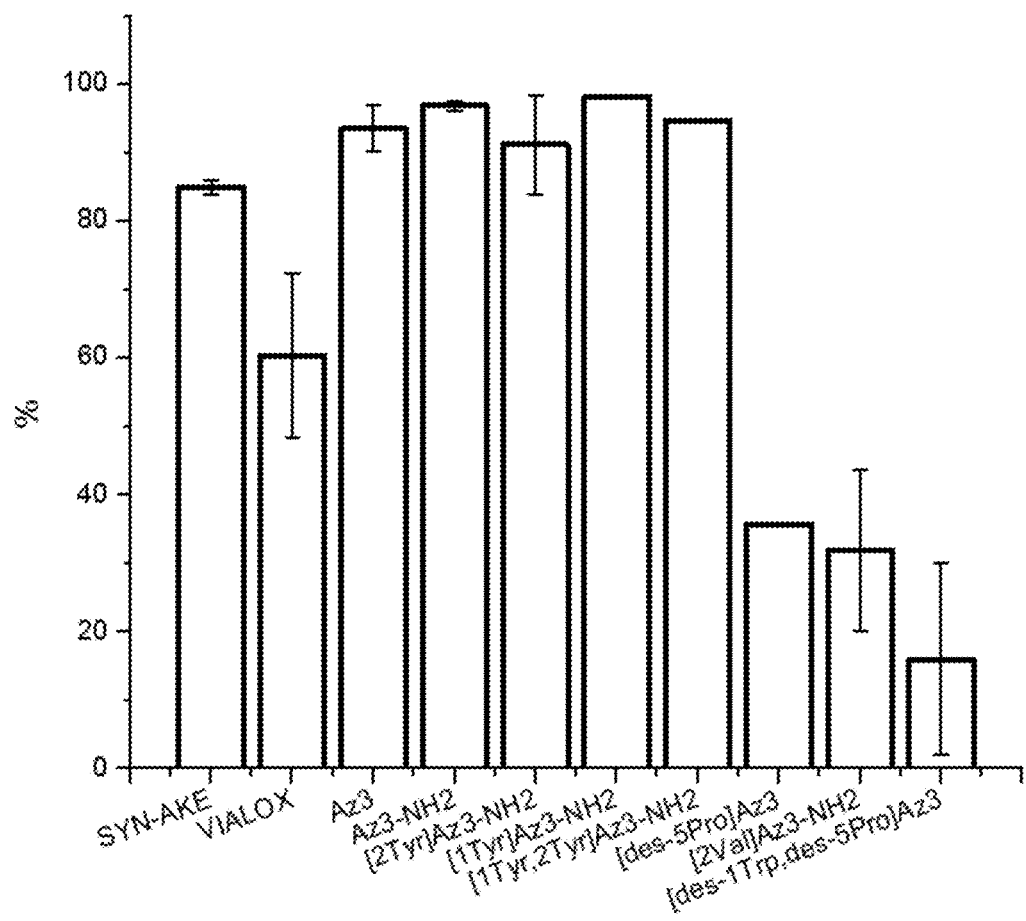
FIG. 3. Comparison of the effectiveness of the current inhibition through the muscle-type nAChR channel by various derivatives of azemiopsin and commercially available compounds Syn-Ake and Vialox. The tested compounds are taken at concentration of 1 mM. 100% refers to complete blockage of the current, 0% refers to the unblocked current in response to application of 20 μM acetylcholine.
Figure 4:
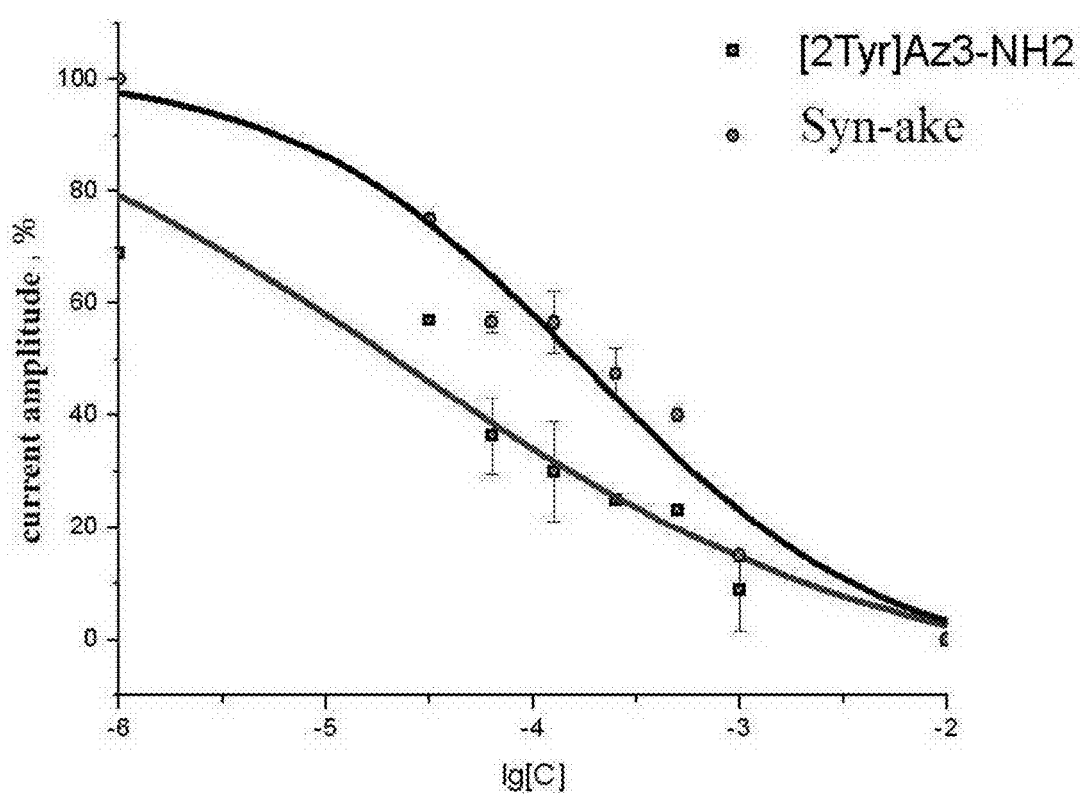
FIG. 4. Comparison of the curves describing dependence of inhibiting activity on concentration for SEQ ID NO:41 ([2Tyr]Az3NH2) and commercial drug Syn-ake. Absciss axis represents decimal logarithm of ligand concentrations, ordinate represents current through receptor channel (% of control) in response to application of 20 μM acetylcholine.
Figure 5:
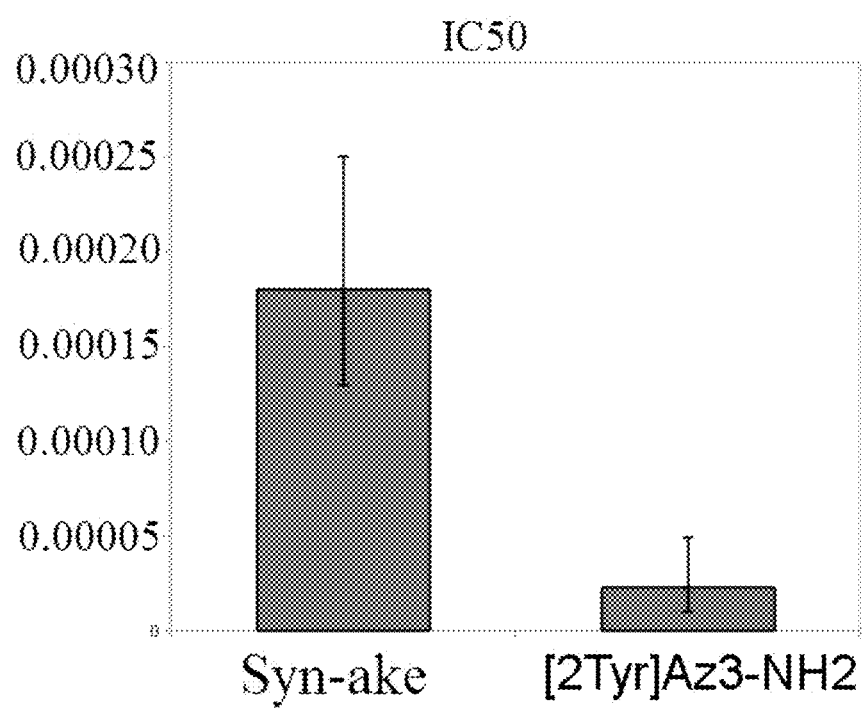
FIG. 5. Comparison of concentrations for half inhibition of the current through the muscle-type nAChR channel. Ordinates represents concentration of tested peptides ([Tyr2]Az3-NH2 и Syn-ake).
Figure 6:
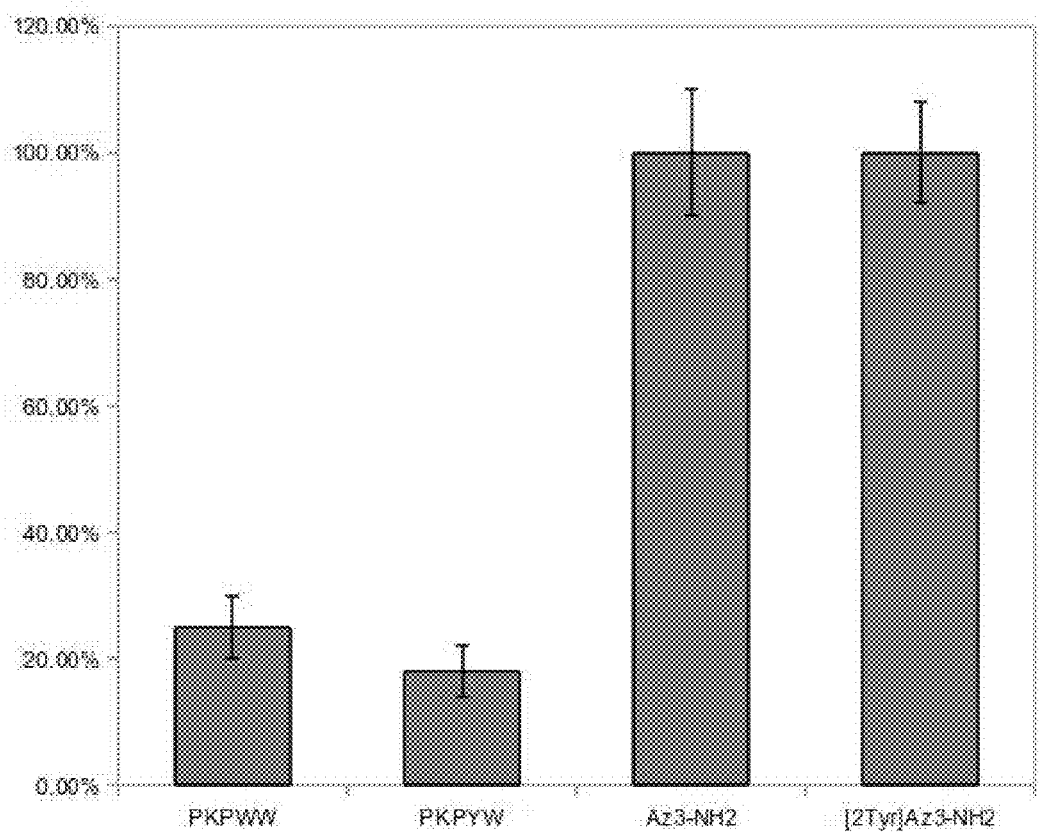
FIG. 6. Comparison of effectiveness of inhibition of the current through the muscle-type nAChR channel by peptides Az3-NH2, [2Tyr]Az3-NH2 and their retro-sequences (SEQ ID NOS 52-53, respectively, in order of appearance) taken at concentration of 1 mM. 100% refers to complete blockage of the current, 0% refers to the control current

Chemical synthesis of peptide SEQ ID NO:1: H-Trp-Trp-Pro-Lys-Pro-OH.

Coupling of the first amino acid to the polymer (P). Preparation of Fmoc-Pro-P (Fmoc=9-fluorenylmethyloxycarbonyl).

200 mg 2-chlorotritylchloride containing 1.0 mmole hydroxyl groups per gram is washed with dry methylene chloride. 374 mg (1.1 mmoles) Fmoc-Pro-OH and 374 μl (2.2 mmole) diisopropylethylamine are dissolved in 5 ml methylene chloride, the solution is stirred 5 min and added to the polymer. The reaction is carried out for one hour at room temperature and stirring. After the end of the reaction, the polymer is filtered and washed with methylene chloride, ethanol and dimethylformamide three times.

Description of one synthetic cycle for elongation of peptide chain.

Preparation of Fmoc-Lys(Boc)-Pro-P:
  a) the peptidyl-polymer obtained as described above is treated with 20% solution of piperidine in dimethylformamide for 20 min. Then the polymer is washed for 2 min with 5 ml dimethylformamide two times, for 5 min with 5 ml dioxane-water mixture (2:1) and five times for 2 min with 5 ml dimethylformamide again.
  b) 505 mg (1.1 mmole) Fmoc-Lys(Boc)-OH, 150 mg 1-hydroxybenzotriazole (1.1 mmoles) and 170 μl (1.1 mmoles) N,N'-diisopropylcarbodiimide are dissolved in 5 mldimethylformamide, the solution is stirred for 10 min at 0° C. and added to the polymer. The reaction is carried out for 4 hours with regular stirring. At the end of the reaction process the polymer is filtered off, washed with dimethylformamide and treated with 5 ml mixture $Ac_2O$-pyridine-dimethylformamide (20:20:60) for one hour, then the polymer is washed with dimethylformamide, isopropanole and again dimethylformamide.

The polypeptide chain synthesis is carried out manually in glass flowing reactor (2×20 cm) using the protocol which follows below for each synthetic cycle (taking 8-10 ml of solvent for 400 mg of starting polymer), when carrying out the reaction of condensation (operation 6). The volume of the reaction mixture is 5-7 ml:

1. DMFA (dimethylformamide)) (5×2 min);
2. 20% piperidine in ДМФА (20 min);
3. DMFA (3×2 min);
4. dioxane-water, 2:1, (2×5 min);
5. DMFA (5×2 min);
6. Condensation reaction: 5 molar equivalents of activated Fmoc-amino acid (4 h);
7. DMFA (3×2 min);
8. acetylation: $Ac_2O$-pyridine-dimethylformamide, 20:20:60, (1 h);
9. DMFA (3×2 min);
10. isopropanole (3×2 min);

To activate Fmoc-amino acid derivatives by DIPCDI/HOBT (N,N'-diisopropylcarbodiimide/1-hydroxybenzotriazole) mixture, 170 µl DIPCDI (1.1 mmoles, 5 equivalents) in 4 ml DMFA are added to the solution of 1.1 mmoles (5 equivalents) of Fmoc-protected aminoacid and 150 mg (1.1 mmoles, 5 equivalents) HOBt in 4 ml DMFA, the solution is stirred for 10 min.

The completeness of condensation reaction after operation 6 of synthetic protocol is controlled by ninhydrin test; in case of N-terminal proline, isatin test is used.

The following amino acid derivatives were used for synthesis: Fmoc-Lys(Boc)-OH, Fmoc-Pro-OH, Fmoc-Trp(Boc)-OH.

Cleavage of peptide from polymer.

For the reaction of peptide cleavage from polymer and simultaneous removal of side chain blocking groups, 800 mg peptidyl-polymer was used. 15 ml mixture of TFA (trifluoroacetic acid) with water (97.5:2.5 V/V) is added to the peptidyl-polymer and suspension is stirred for 2 hours, then the solution of the peptide obtained is filtered of the polymer, the polymer is washed with 5 ml TFA, and extra TFA is removed from combined solution by evaporation under reduced pressure. The peptide is precipitated by addition of 100 ml of ethyl ester, filtered and washed with the ester (5×20 ml). Precipitate is dissolved in 5 ml 10% acetic acid for 20 min, filtered and the residue was washed with 5 ml 10% acetic acid. The peptide solution obtained is freeze-dried and desalted by gel-filtration on the Sephadex G-10 column (2.5×60 sm) equilibrated with 0.1 M acetic acid. The peptide is purified by means of reversed-phase HPLC using a gradient of acetonitrile in water (from 10% to 35% in 75 min) in the presence of 0.1% acetic acid at the flow rate 3 ml/min, eluate absorbance is detected at 226 nm. The fractions corresponding to the main absorbance peak are collected and freeze-dried. The molecular mass of the peptide determined by mass-spectrometry is 713.8 Da, calculated molecular mass—712.8 Da.

EXAMPLE 2

Estimation of acute toxicity for peptide H-Trp-Trp-Pro-Lys-Pro-OH (SEQ ID NO: 1).

Estimation of acute toxicity ($LD_{50}$) after intraperitoneal administration of peptide H-Trp-Trp-Pro-Lys-Pro-OH (SEQ ID NO: 1) was carried out on 40 male Balb mice weighting 20-23 g, separated into five equal groups. Mice were intraperitoneally injected with the peptide at doses of 1 mg/kg, 3 mg/kg, 10 mg/kg and 30 mg/kg in 0.2 ml sterile 0.9% NaCl solution. Control animals were injected with same volume of 0.9% NaCl. The results of the experiments did not reveal any toxic effects of the peptide for any of the tested groups.

Investigation of acute toxicity ($LD_{50}$ per os) after administration of the peptide directly into a stomach by a special catheter was conducted on 40 male Balb mice weighting 20-23 g. Animals were randomly divided into 5 groups. The drug was applied at doses 2.5 mg/kg, 10 mg/kg, 40 mg/kg, 160 mg/kg in 0.2 ml sterile solution of 0.9%. Control animals were injected with the same volume of 0.9% NaCl. After the administration of the studied peptide at concentrations given above into the stomach of the mice, no toxic effect was observed.

EXAMPLE 3

Preparation of the cream containing peptide H-Trp-Trp-Pro-Lys-Pro-OH (SEQ ID NO: 1) with the range of concentrations between 0.01 and 5%. Cream composition: H-Trp-Trp-Pro-Lys-Pro-OH (SEQ ID NO: 1)-0.01%, 1% or 5%, glycerin-20%, stearic acid-2%, butylparaben-1%, glyceryl stearate-1%, stearyl alcohol-2%, decyl oleate-3%, water up to 100%. All the ingridients except water and peptide H-Trp-Trp-Pro-Lys-Pro-OH (SEQ ID NO: 1), are mixed and heated up to 70° C. till homogeneous clear mass is obtained. Then the mixture is cooled up to 40° C., and water solution of peptide H-Trp-Trp-Pro-Lys-Pro-OH (SEQ ID NO: 1) is added to the mixture at constant stirring. The cream is cooled down slowly to the room temperature.

EXAMPLE 4

Investigation of skin-irritating action of the preparation. The skin-irritating action was tested in two ways. In an acute single treatment, and subacute repeated daily treatment within 2 weeks, experiments were conducted on five healthy volunteers (3 women (aged 24, 29 and 51) and 2 men (aged 44 and 46). The cream samples containing 0.01%, 1% or 5% tested peptide were administered daily within two weeks on the area of a forehead and a forearm. Skin-irritating activity was observed neither under single exposure nor under sequential administration of the cosmetics.

EXAMPLE5

Electrophysiological studies were carried out on muscle-type nicotinic acetylcholine receptors (nAChRs) heterolitically expressed in oocytes from clawed frog *Xenopus laevis*. Adult clawed frog (no less than 8 cm size) was placed into the solution of p-aminobenzoic acid for 15-20 minutes till total immobilization. For taking the necessary amount of oocytes, incision of skin and abdominal muscle layer of the frog was made laterally to <<bikini line>> and a portion of ovary was exteriorized. Exteriorized portion of ovary was settled into ND96 buffer without potassium ions and was minced. If necessary, oocytes were additionally treated with collagenase solution. The post-surgical cuts on the animal were sewed using suture material from polyglycolide. Each clawed frog was operated no more than once in 6 weeks.

Expression of the receptor was performed using the following procedure: solution of the mixure of the plasmids containing inserts with processed genes of $\alpha1$, $\beta1$, $\delta$ and $\epsilon$-subunits of the muscle-type nAChR under CMV-promotor control were injected into nucleus of freshly prepared oocytes using Nanotech (<<Drummond scientific>>, USA) device, after which oocytes were incubated at 18° C. for 48 hours.

The nAChR is a ligand-gated ionic channel. After binding with the agonist (acetylcholine or nicotine), the receptor sustains conformational changes as a result of which positively charged ions go through the open ion channel. As soon as electrodes are attached to cell membrane expressing the receptor the possibility to record ionic current through the opening receptor channels appears.

Oocytes were placed into the tank with electrodes connected with the amplifier Turbo-TEC 03× (NPI Electronics, USA); the tank had preliminary been filled up with buffer ND96. The experiments were carried out using two-electrode fixation potential configuration. Amplifier electrodes made from borosilicate glass and filled with 3 M KCl, were injected into an oocyte. Membrane potential was fixed at −70 mV. Oocytes expressing muscle-type nAChR were treated with 20 µM acetylcholine several times for 5 min until the current amplitude reached the stationary level in response to acetylcholine application. Then, oocyte were incubated for 5-minute in the solution of the peptide tested. After five-minute incubation with the peptide, an oocyte was treated with 20 μM acetylcholine solution in the presence of the peptide. The experiments were repeated using different concentrations of the peptides tested on several oocytes from different preparations. The amplitude of the current in response to application of acetylcholine in the presence of the peptide tested was compared with the amplitude of the current in response to the control application (in the absence of the peptide) carried out before each experiment. Dependence of current amplitude (represented as percentage of control) on decimal logarithm of ligand concentration was built to reveal characteristics of the peptide tested. Estimation of the inhibition curves and values of EC50 was performed using the program Origin 7.5 and the <<dose response>> model.

The invention claimed is:

1. A cosmetic composition for smoothing facial and age-related wrinkles, comprising a compound of the general formula (I): X1-X2-X2-Pro-X4-Pro-X5 (SEQ ID NO:54), wherein:
    X1 is selected from the group consisting of H—, Ac—, and Palm-;
    X2 is selected from the group consisting of Trp, and Tyr;
    X3 is selected from the group consisting of Trp, and Tyr;
    X4 is selected from the group consisting of Lys, Orn, Dbu, Dpr, and Arg; and
    X5 is selected from the group consisting of —OH, —NH$_2$, —OCH$_3$, —OC$_2$H$_5$, and —NHC$_6$H$_5$;
    or a cosmetically acceptable retro-isomer and/or salt thereof;
    wherein the compound is present in an amount effective to selectively block muscle-type nicotinic acetylcholine receptors and suitable for smoothing facial and age-related wrinkles; and
    wherein the cosmetic composition is in the form of a lotion, balm, cream, gel, gel forming polymers, spray, or face mask.

2. The cosmetic composition of claim 1, wherein X1 is Ac— (SEQ ID NO:55).

3. The cosmetic composition of claim 1, wherein X5 is —NH$_2$ (SEQ ID NO:56).

4. The cosmetic composition of claim 1, wherein X2 and X3 are both -Trp- or -Tyr-, and X4 is -Lys- or -Dbu- (SEQ ID NO:57).

5. The cosmetic composition of claim 1, wherein the compound of general formula (I) has an amino acid sequence identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, or SEQ ID NO:48.

6. A method of blocking neuromuscular transmission in a human subject, comprising:
    (a) topically administering the cosmetic composition of claim 1 to a human subject in need thereof; and
    (b) blocking neuromuscular transmission in the human subject;
    wherein the cosmetic composition blocks muscle-type nicotinic acetylcholine receptors in at least one muscle cell of the human subject.

7. The cosmetic composition of claim 1 wherein the compound of general formula (I) is present in a weight concentration ranging from 0.01 to 5%.

8. The cosmetic composition of claim 1, further comprising at least one additional component selected from the group consisting of amino acids, proteins, protein hydrolysates, growth factors, enzymes, enzyme inhibitors, peptides, oligosaccharides, polysaccharides, pyrimidines, purines, nucleotides, nucleosides, carboxylic acids, fat acids, alcohols, lipids, sphingolipids, flavonoids, terpenes, alkaloids, benzofurans, polyalcohols, antimicrobial component, antimicrobial peptides, vitamins, provitamins, retinoids, carotenoids, chelating agents, antioxidants, and agents that enhance skin permeability.

9. The cosmetic composition of claim 1, further comprising a dermatologically acceptable carrier.

10. The cosmetic composition of claim 1, wherein the composition comprises a solution, a dispersion, an emulsion, or liposomes.

* * * * *

SEQUENCE LISTING

```
<160> NUMBER OF SEQ ID NOS: 72

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OH

<400> SEQUENCE: 1

Trp Trp Pro Lys Pro
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OH

<400> SEQUENCE: 2

Trp Tyr Pro Lys Pro
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OH

<400> SEQUENCE: 3

Tyr Trp Pro Lys Pro
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OH

<400> SEQUENCE: 4

Tyr Tyr Pro Lys Pro
1               5

<210> SEQ ID NO 5
```

```
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OH

<400> SEQUENCE: 5

Trp Trp Pro Xaa Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OH

<400> SEQUENCE: 6

Trp Tyr Pro Xaa Pro
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OH

<400> SEQUENCE: 7

Tyr Trp Pro Xaa Pro
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OH

<400> SEQUENCE: 8

Tyr Tyr Pro Xaa Pro
1               5
```

```
<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OH

<400> SEQUENCE: 9

Trp Trp Pro Lys Pro
1               5

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OH

<400> SEQUENCE: 10

Trp Tyr Pro Lys Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OH

<400> SEQUENCE: 11

Tyr Trp Pro Lys Pro
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OH

<400> SEQUENCE: 12

Tyr Tyr Pro Lys Pro
1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OH

<400> SEQUENCE: 13
```

Trp Trp Pro Xaa Pro
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OH

<400> SEQUENCE: 14

Trp Tyr Pro Xaa Pro
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OH

<400> SEQUENCE: 15

Tyr Trp Pro Xaa Pro
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OH

<400> SEQUENCE: 16

Tyr Tyr Pro Xaa Pro
1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term NH2

<400> SEQUENCE: 17

Trp Trp Pro Lys Pro
1               5

```
<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term NH2

<400> SEQUENCE: 18

Trp Tyr Pro Lys Pro
1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term NH2

<400> SEQUENCE: 19

Tyr Trp Pro Lys Pro
1               5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term NH2

<400> SEQUENCE: 20

Tyr Tyr Pro Lys Pro
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term NH2

<400> SEQUENCE: 21

Trp Trp Pro Xaa Pro
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (4)..(4)
<223> OTHER INFORMATION: Dbu
<220> FEATURE:
<223> OTHER INFORMATION: N-term Ac; C-term NH2

<400> SEQUENCE: 22

Trp Tyr Pro Xaa Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term NH2

<400> SEQUENCE: 23

Tyr Trp Pro Xaa Pro
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term NH2

<400> SEQUENCE: 24

Tyr Tyr Pro Xaa Pro
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OCH3

<400> SEQUENCE: 25

Trp Trp Pro Lys Pro
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OCH3

<400> SEQUENCE: 26
```

Trp Tyr Pro Lys Pro
1               5

<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OCH3

<400> SEQUENCE: 27

Tyr Trp Pro Lys Pro
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term OCH3

<400> SEQUENCE: 28

Tyr Tyr Pro Lys Pro
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OCH3

<400> SEQUENCE: 29

Trp Trp Pro Xaa Pro
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OCH3

<400> SEQUENCE: 30

Trp Tyr Pro Xaa Pro
1               5

<210> SEQ ID NO 31
<211> LENGTH: 5
<212> TYPE: PRT

<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OCH3

<400> SEQUENCE: 31

Tyr Trp Pro Xaa Pro
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term OCH3

<400> SEQUENCE: 32

Tyr Tyr Pro Xaa Pro
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OCH3

<400> SEQUENCE: 33

Trp Trp Pro Lys Pro
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OCH3

<400> SEQUENCE: 34

Trp Tyr Pro Lys Pro
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OCH3

```
<400> SEQUENCE: 35

Tyr Trp Pro Lys Pro
1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term OCH3

<400> SEQUENCE: 36

Tyr Tyr Pro Lys Pro
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OCH3

<400> SEQUENCE: 37

Trp Trp Pro Xaa Pro
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OCH3

<400> SEQUENCE: 38

Trp Tyr Pro Xaa Pro
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OCH3

<400> SEQUENCE: 39

Tyr Trp Pro Xaa Pro
```

```
1               5
```

```
<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term Ac; C-term OCH3

<400> SEQUENCE: 40

Tyr Tyr Pro Xaa Pro
1               5

<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term NH2

<400> SEQUENCE: 41

Trp Trp Pro Lys Pro
1               5

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term NH2

<400> SEQUENCE: 42

Trp Tyr Pro Lys Pro
1               5

<210> SEQ ID NO 43
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term NH2

<400> SEQUENCE: 43

Tyr Trp Pro Lys Pro
1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term H; C-term NH2

<400> SEQUENCE: 44

Tyr Tyr Pro Lys Pro
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term NH2

<400> SEQUENCE: 45

Trp Trp Pro Xaa Pro
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term NH2

<400> SEQUENCE: 46

Trp Tyr Pro Xaa Pro
1               5

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
<220> FEATURE:
<223> OTHER INFORMATION: N-term H; C-term NH2

<400> SEQUENCE: 47

Tyr Trp Pro Xaa Pro
1               5

<210> SEQ ID NO 48
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Dbu
```

```
<220> FEATURE:
<223> OTHER INFORMATION: N-term H; C-term NH2

<400> SEQUENCE: 48

Tyr Tyr Pro Xaa Pro
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Ac; C-term NH2

<400> SEQUENCE: 49

Glu Glu Met Gln Arg Arg
1               5

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H; C-term NH2

<400> SEQUENCE: 50

Gly Pro Arg Pro Ala
1               5

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Asn Trp Trp Pro Lys Pro Pro His Gln Gly Pro Arg Pro Pro Arg
1               5                   10                  15

Pro Arg Pro Lys Pro
            20

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Pro Lys Pro Trp Trp
1               5

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 53

Pro Lys Pro Tyr Trp
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Trp or Tyr
<220> FEATURE:
<221> NAME/KEY: MOD_RES
<222> LOCATION: (4)..(4)
<223> OTHER INFORMATION: Lys, Orn, Dbu, Dpr or Arg
<220> FEATURE:
<223> OTHER INFORMATION: N-term may or may not be modified by H-, Ac- or
      Palm-; C-term may or may not be modified by -OH, -NH2, -OCH3,
      -OC2H5 or -NH-C6H5; See specification as filed for detailed
      description of substitutions and preferred embodiments

<400> SEQUENCE: 54

Xaa Xaa Pro Xaa Pro
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ac-Trp or Ac-Tyr
<220> FEATURE:
<221> NAME/KEY: MOD_RES
<222> LOCATION: (2)..(2)
<223> OTHER INFORMATION: Trp or Tyr
<220> FEATURE:
<221> NAME/KEY: MOD_RES
<222> LOCATION: (4)..(4)
<223> OTHER INFORMATION: Lys, Orn, Dbu, Dpr or Arg
<220> FEATURE:
<223> OTHER INFORMATION: C-term may or may not be modified by -OH, -NH2,
      -OCH3, -OC2H5 or -NH-C6H5; See specification as filed for detailed
      description of substitutions and preferred embodiments

<400> SEQUENCE: 55

Xaa Xaa Pro Xaa Pro
1               5

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Trp or Tyr;
<220> FEATURE:
<221> NAME/KEY: MOD_RES
<222> LOCATION: (4)..(4)
<223> OTHER INFORMATION: Lys, Orn, Dbu, Dpr or Arg

```
<220> FEATURE:
<221> NAME/KEY: MOD_RES
<222> LOCATION: (5)..(5)
<223> OTHER INFORMATION: Pro-NH2
<220> FEATURE:
<223> OTHER INFORMATION: N-term may or may not be modified by H-, Ac- or
      Palm-; See specification as filed for detailed description of
      substitutions and preferred embodiments

<400> SEQUENCE: 56

Xaa Xaa Pro Xaa Pro
1               5

<210> SEQ ID NO 57
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Trp or Tyr
<220> FEATURE:
<221> NAME/KEY: MOD_RES
<222> LOCATION: (4)..(4)
<223> OTHER INFORMATION: Lys or Dbu
<220> FEATURE:
<223> OTHER INFORMATION: N-term may or may not be modified by H-, Ac- or
      Palm-; C-term may or may not be modified by -OH, -NH2, -OCH3,
      -OC2H5 or -NH-C6H5; See specification as filed for detailed
      description of substitutions and preferred embodiments

<400> SEQUENCE: 57

Xaa Xaa Pro Xaa Pro
1               5

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Asn Trp Trp Pro Lys
1               5

<210> SEQ ID NO 59
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Trp Pro Lys Pro Pro
1               5

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Pro Lys Pro Pro His
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Pro Pro His Gln
1               5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Pro His Gln Gly
1               5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro His Gln Gly Pro
1               5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Gln Gly Pro Arg
1               5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gly Pro Arg Pro
1               5

<210> SEQ ID NO 66
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Gly Pro Arg Pro Pro
1               5

<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Arg Pro Pro Arg
1               5

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Pro Pro Arg Pro
1               5

<210> SEQ ID NO 69
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Pro Pro Arg Pro Arg
1               5

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Arg Pro Arg Pro
1               5

<210> SEQ ID NO 71
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Pro Arg Pro Lys
1               5
```

```
<210> SEQ ID NO 72
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Arg Pro Lys Pro
1               5
```